(12) United States Patent
Hill

(10) Patent No.: US 8,071,140 B2
(45) Date of Patent: Dec. 6, 2011

(54) COMPOSITIONS AND METHODS FOR TREATMENT OF DERMAL SCARRING AND WRINKLING

(76) Inventor: Patricia J. Hill, New York, NY (US)

( * ) Notice: Subject to any disclaimer, the term of this patent is extended or adjusted under 35 U.S.C. 154(b) by 0 days.

(21) Appl. No.: 12/178,597

(22) Filed: Jul. 23, 2008

(65) Prior Publication Data

US 2008/0292734 A1 Nov. 27, 2008

Related U.S. Application Data

(63) Continuation-in-part of application No. PCT/US2007/061006, filed on Jan. 24, 2007.

(60) Provisional application No. 60/761,627, filed on Jan. 24, 2006.

(51) Int. Cl.
*A61K 36/68* (2006.01)
*A61K 36/886* (2006.01)

(52) U.S. Cl. ........................ 424/738; 424/744

(58) Field of Classification Search .................. None
See application file for complete search history.

(56) References Cited

U.S. PATENT DOCUMENTS

| | | | |
|---|---|---|---|
| 5,578,312 A | 11/1996 | Parrinello | |
| 5,738,850 A | 4/1998 | Hendricks et al. | |
| 5,997,876 A | 12/1999 | Shikhashvili et al. | |
| 6,027,716 A * | 2/2000 | Levin et al. | 424/58 |
| 6,197,305 B1 * | 3/2001 | Friedman et al. | 424/737 |
| 6,342,208 B1 | 1/2002 | Hyldgaard et al. | |
| 6,514,540 B1 * | 2/2003 | Sobczak | 424/738 |
| 6,544,530 B1 * | 4/2003 | Friedman | 424/400 |
| 6,576,269 B1 * | 6/2003 | Korneyev | 424/725 |
| 6,770,286 B1 | 8/2004 | Berry | |
| 7,357,950 B2 | 4/2008 | Mazzio et al. | |
| 2004/0109872 A1 | 6/2004 | Villani | |
| 2005/0049206 A1* | 3/2005 | Gong et al. | 514/27 |
| 2005/0136079 A1 | 6/2005 | Burangulov et al. | |

FOREIGN PATENT DOCUMENTS

| | | | |
|---|---|---|---|
| DE | 20112636 | * | 1/2002 |
| RU | 2089178 | * | 9/1997 |
| WO | 0072860 A1 | | 12/2000 |

* cited by examiner

*Primary Examiner* — Christopher R. Tate
(74) *Attorney, Agent, or Firm* — Pryor Cashman LLP; Andrew S. Langsam

(57) ABSTRACT

Compositions and methods for treatment of dermal scarring and wrinkling, by application to the skin of a cosmetically effective amount of *Plantago major* or *Plantago Lanceolata*. The plantain may be utilized in powdered form in an aqueous paste or poultice, or in a crème base or ointment that is applied to the skin for various periods of time from 1 to 10 hours at a frequency of 1-12 times per week, for a period of 3-50 weeks or more. The composition is effective to remediate dermal scarring and wrinkling, and at least partially restore skin to an undamaged, undeteriorated state.

12 Claims, 8 Drawing Sheets

COMPOSITIONS AND METHODS FOR TREATMENT OF DERMAL SCARRING AND WRINKLING

CROSS-REFERENCE TO RELATED APPLICATIONS

This application is a continuation-in-part, filed under the provisions of 35 USC 120, of International Patent Application PCT/US2007/61006 filed Jan. 24, 2007 in the name of Patricia J. Hill, which in turn claims the benefit of priority under 35 USC 119 of U.S. Provisional Patent Application 60/761,627 filed Jan. 24, 2006 in the name of Patricia J. Hill for "COMPOSITIONS AND METHODS FOR TREATMENT OF DERMAL SCARRING AND WRINKLING." The disclosures of said international patent application and said provisional application are hereby incorporated herein by reference in their respective entireties, for all purposes.

FIELD OF THE INVENTION

The present invention relates to compositions and method for remediating dermal scarring and wrinkling, to at least partially restore skin to an undamaged, undeteriorated state.

DESCRIPTION OF THE RELATED ART

In the field of skin care, numerous products have been developed for cosmetic treatment of skin to reverse or ameliorate skin damage, including moisturizers, cleansers, dermal abrasives, dermal growth factors, liposomes, plant and animal extracts, essential oils and a wide variety other ingredients.

In this field, cosmetics have been proposed that are based on various natural raw materials, which are used to treat skin and counter the ageing processes. Compositions of such type are described, for example, in U.S. Patent Application Publication No. 20060002884.

In addition, although the art has contemplated various compositions to ameliorate skin wrinkling incident to aging, lesser attention has been devoted to remediation of skin that has been scarred, e.g., as a result of laceration, abrasion, ulceration or other skin injury.

U.S. Patent Application Publication No. 20050276766 describes a method for stimulating the remodeling of a skin blemish in a warm-blooded animal comprising administering to the skin blemish a composition that comprises an ionic metal-peptide complex and a salicylate in an amount effective to diminish or remove the skin blemish, in which the skin blemish may include a skin tag, acne scar, skin callus, benign skin mole, stretch mark, solar keratosis, keloid scar, burn scar, thickened sunspot, or surgical scar.

The art continues to seek improvements in compositions and methods of skin treatment to combat wrinkling as well as scarring of the skin.

SUMMARY OF THE INVENTION

The present invention relates to treatment of skin to at least partially ameliorate scarring and/or wrinkling.

In one aspect, the invention relates to a method for cosmetically treating skin to reduce scarring and/or wrinkling, the method comprising topically applying to an affected skin area a cosmetically effective amount of plantain (*Plantago major* or *Plantago Lanceolata*).

In another aspect, the invention relates to a composition comprising a cosmetically effective amount of plantain (*Plantago major* or *Plantago Lanceolata*) in an aqueous paste formulation including at least one ingredient selected from among humectants, antioxidants, petroleum jelly, vitamins and menthol.

A further aspect of the invention relates to an ointment useful for treatment of burns, comprising plantain, *Aloe Barbadensis* leaf juice, sunflower oil, Shea butter and tocopherol.

A still further aspect of the invention relates to an ointment useful for treatment of burns, comprising plantain, *Aloe Barbadensis* leaf juice, sunflower oil, Shea butter and tocopherol, and one or more additives selected from the group consisting of cocoa butter, avocado oil, *Arnica Montana* flower extract, *Gardenia Tahitensis* flower, beeswax, Bisabolol, clove oil, and menthol camphor.

The plantain composition of the invention in one embodiment comprises water, glycerin and plantain, and at least one of the following components: modified cornstarch, emulsifying wax, lactose, urea, *Helianthus Annuus* (hybrid sunflower) oil, *Butyrospermum Parkii* (Shea butter) Fruit, *Theobroma cacao* (cocoa) seed butter, *Arnica Montana* flower extract, *Aloe Barbadensis* leaf juice, Bisabolol, *Cocos Nucifera* (coconut) oil, *Gardenia Tahitensis* flower, *Glycine soja* (soybean) oil, *Ribee Nigrum* (black current) seed oil, Sucrose Cocoate, *Glycine soja* (soybean) sterol, tocopherol, tocopheryl acetate, disodium EDTA, sorbitan stearate, PEG-40 stearate, phenoxyethanol, butylparaben, ethylparaben, methylparaben and propylparaben.

The plantain compositions of the invention include plantain compositions comprising an ointment formulation containing an extract derived from a plantain powder, and ointment formulations containing plantain in a particulate form.

Another aspect of the invention relates to a plantain composition comprising plantain or an extract thereof, and at least one antibiotic, e.g., polymixin B sulfate, bacitracin zinc and/or neomycin.

The invention in another aspect relates to a plantain composition including a cream base and plantain or plantain extract.

In a further aspect, the invention relates to a method of making a dermatological plantain composition, comprising dispersing plantain powder in an aqueous medium and mixing the resulting material for a predetermined time at elevated temperature to cause extraction of the plantain into the aqueous medium, recovering a supernatant from said material, and formulating the supernatant with a dermatologically acceptable carrier to produce said dermatological plantain composition.

Yet another aspect of the invention relates to a plantain cream composition, comprising the following ingredients in the specified weight percentages:

Water, 50-70 weight percent
Lactose, 0.5-5 weight percent
Urea, 0.5-5 weight percent
*Aloe Barbadensis* Leaf Juice, 0-0.1 weight percent
Disodium EDTA, 0-0.2 weight percent
Sodium Carboxymethyl Starch, 0-2 weight percent
Glycerin, 10-25 weight percent
DL-alpha Tocopheryl Nicotinate, 0-1 weight percent
Self-Emulsifying Wax NF, 0-6 weight percent
*Glycine Soja* (soybean) Oil (and) *Helianthus Annuus* (Hybrid Sunflower) Oil, 0-4 weight percent
Tocopheryl Acetate, 0-1 weight percent
*Butyrospermum Parkii* (Shea Butter) Fruit, 0-4 weight percent
*Cocos Nucifera* (Coconut) Oil, 0-4 weight percent
*Cocos Nucifera* (Coconut) Oil/*Aloe Barbadensis* Leaf Extract, 0-4 weight percent

*Glycine Soja* (Soybean) Oil (and) *Arnica Montana* Flower Extract (and) Tocopherol, 0-4 weight percent Bisabolol, 0-1 weight percent Hydrogenated Coconut Oil (and) *Gardenia Tahitensis* Flower (and) Tocopherol, 0.5-2.5 weight percent

*Oenothera Biennis* (Evening Primerose) Flower Oil, 0.1-1 weight percent

Camelina Oil, 0.1-1 weight percent

Benzyl PCA (and) Phenoxyethanol, 0.2-2 weight percent

*Plantago Major* Leaf, 0.1-5 weight percent

Mica (and) Titanium Dioxide (and) Iron Oxides, 0-2 weight percent wherein the weight percent of all ingredients totals to 100 weight percent.

An additional aspect of the invention relates to a plantain cream composition, comprising the following ingredients in the specified weight percentages:

| Ingredient | Wt % |
| --- | --- |
| Water | 50-65 |
| Lactose | 0-5 |
| Urea | 0-5 |
| *Aloe Barbadensis* Leaf Juice | 0-0.5 |
| Disodium EDTA | 0-0.5 |
| Sodium Carboxymethyl Starch | 0-2.5 |
| Glycerin | 8-22 |
| DL-alpha Tocopheryl Nicotinate | 0-2 |
| Self-Emulsifying Wax NF | 0-5 |
| *Glycine Soja* (soybean) Oil (and) *Helianthus Annuus* (Hybrid Sunflower) Oil | 0-5 |
| Tocopheryl Acetate | 0-2 |
| *Butyrospermum Parkii* (Shea Butter) Fruit | 0-5 |
| *Cocos Nucifera* (Coconut) Oil | 0-5 |
| *Prunus Amygdalus Dulcis* (Sweet Almond) Oil (and) Hydrogenated Vegetable Oil | 0-5 |
| *Glycine Soja* (Soybean) Oil (and) *Arnica Montana* Flower Extract (and) Tocopherol | 0-5 |
| Bisabolol | 0-0.5 |
| Hydrogenated Coconut Oil (and) *Gardenia Tahitensis* Flower (and) Tocopherol | 0-2.5 |
| *Oenothera Biennis* (Evening Primerose) Flower Oil | 0-1.5 |
| Jojoba Oil | 0-2 |
| Benzyl PCA (and) Phenoxyethanol | 0-2.5 |
| *Plantago Major* Leaf | 0.5-10 |
| Mica (and) Titanium Dioxide (and) Iron Oxides | 0-5 | wherein the weight percent of all ingredients totals to 100 weight percent.

The invention relates in another aspect to a plantain ointment composition, comprising the following ingredients in the specified weight percentages:

| Ingredient | Wt % |
| --- | --- |
| Purified Water | 25-50 |
| Glycerin | 8-26 |
| Lactose | 0-5 |
| Urea | 0-5 |
| Sucrose Cocoate | 0-2.5 |
| *Aloe Barbadensis* Leaf Juice | 0-0.5 |
| *Butyrospermum Parkii* (Shea Butter) Fruit | 0-4 |
| *Theobroma Cacao* (Cocoa) Seed Butter | 0-4 |
| *Helianthus Annuus* (Hybrid Sunflower) Oil | 0-4 |
| Tocopheryl Acetate | 0-1.5 |
| Self-Emulsifying Wax | 0-10.5 |
| *Glycine Soja* (Soybean) Oil & *Arnica Montana* Flower Extract & Tocopherol | 0-5 |
| *Glycine Soja* (Soybean) Sterol | 0-2 |
| *Plantago Lanceolata* Leaf Extract | 2-20 |
| Disodium EDTA | 0-0.5 |
| Bisabolol | 0-0.5 |
| Phenoxyethanol, Methylparaben, Ethylparaben, Propylparaben, Butylparaben | 0-5 |
| Hydrogenated Coconut Oil & *Gardenia Tahitensis* Flower & Tocopherol | 0-5 |
| Sorbitan Stearate | 0-2.5 |
| PEG-40 Stearate | 0-2.5 |
| *Ribes Nigrum* (Black Currant) Seed Oil | 0-4 |
| Corn Starch Modified | 0-15 | wherein the weight percent of all ingredients totals to 100 weight percent.

Additional aspects of the invention relate to the use of such ointments and compositions for treatment of skin to ameliorate skin damage.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
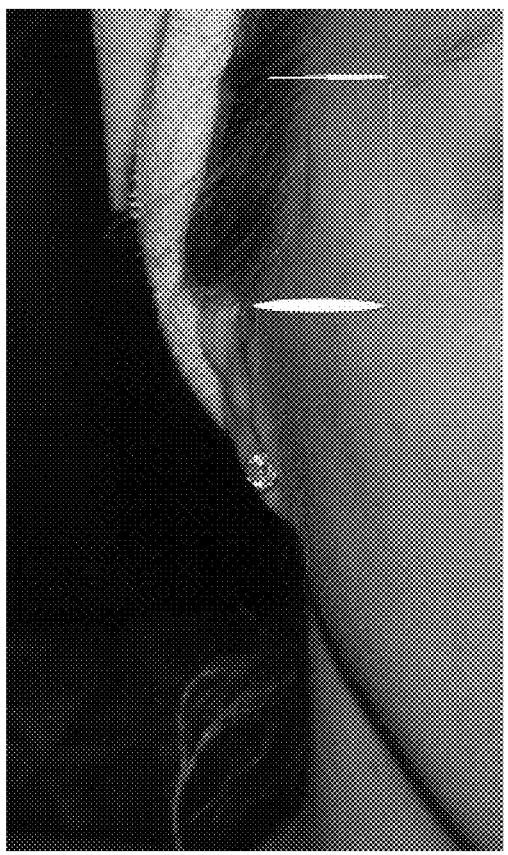
FIG. 1 is a photograph of a hypertrophic 10-year-old facial scar at the right temple of the illustrated individual, as it appeared prior to treatment with a composition according to the present invention.

The present invention relates to compositions and methods for remediating dermal scarring and wrinkling, to at least partially restore skin to an undamaged, undeteriorated state.

Although plantain plants and extracts have been used in the prior art for treatment of wounds, incisions and other skin penetration events, for healing thereof, e.g., as taught by U.S. Pat. No. 5,192,542, (teaching use of plantain in a product for treating tissue to form closures of wounds, incisions, and other openings, particularly during the embalming process), the art has previously failed to recognize that plantain has a substantial therapeutic effect in application to remediating dermal scarring and wrinkling, so that the skin is at least partially restored to an undamaged, undeteriorated state.

I have discovered that plantain, including plant parts and extracts therefrom, can be usefully employed to ameliorate the visible character of scarring and wrinkling, in a highly efficient manner.

The plantain plant employed in the practice of my invention is *Plantago major* or *Plantago Lanceolata*, and such plant may be used in any suitable form, including powdered (lyophilized) form, or as a whole fresh plant, or plant parts, e.g., leaves, stems, etc., or as an extract, e.g., juice, from the plant, or as a soft pulp that is made by chopping, osterizing, etc. the plant or plant parts. In one embodiment, the plantain, in powder or pulp form, is mixed with water to form a poultice that then is applied to the afflicted skin area.

For extraction of plantain, the plantain leaves can be harvested and thoroughly washed and rinsed. After the plantain leaves are washed and rinsed, they can be ground or chopped to create a soft pulp, or dried and pulverized to form a powder, or lyophilized in a vacuum chamber and then used in whole or finely divided form.

In one embodiment, a pulp may be formed from the leaves and used in such form, or the pulp alternatively can be subjected to extraction or juicing to produce an extract or juice that is useful in compositions of the invention. Other extract forms of plantain can be used.

In a particularly preferred embodiment, the plantain is used in powdered form, as part of an aqueous formulation that then is applied to the afflicted area as part of a regimen of therapeutic intervention.

By use of plantain compositions of the invention, applied to the afflicted area of the skin on an ongoing basis at regular intervals, scarring and/or wrinkling of the skin can be at least partially reversed, to achieve an enhanced cosmetic effect.

In one embodiment of the invention, the plantain is utilized in powder form, commercially available from Mountain Rose Herbs, Eugene, Oreg., www.mountainroseherbs.com as *Plantago major* powder.

The efficacy of compositions of the invention has been demonstrated for diminishment of skin wrinkling, in which skin creases, folds, laugh lines and the like have been demonstrated to have been significantly reduced in visual prominence by the treatment with the compositions of the invention. Treatments for wrinkle reduction may involve application to the wrinkled skin areas of a composition containing 40-60% weight of *Plantago major* powder in water, based on the total weight of the composition, or, more preferably, a 100% *Plantago major* powder administration to the wrinkled area, as a dry powder composition that may be held in place by a bandage, mask, eye cup, or the like.

In specific embodiments of the invention, aqueous compositions containing *Plantago major* powder in amounts of from 50 to 100 weight %, based on the total weight of the composition containing the *Plantago major* powder and water, can be advantageously employed, it being recognized that the relative amount and ingredients of the composition can be varied widely within the scope of the invention. For example, the amount of plantain in a dermatological treatment composition of the invention can range from amounts as low as 0.1% by weight, based on the weight of the composition, to amounts approaching 100% by weight of the composition.

The invention in a specific aspect relates to a plantain composition including water, glycerin and plantain, and at least one of the following components: modified cornstarch, emulsifying wax, lactose, urea, *Helianthus Annuus* (hybrid sunflower) oil, *Butyrospermum Parkii* (Shea butter) Fruit, *Theobroma cacao* (cocoa) seed butter, *Arnica Montana* flower extract, *Aloe Barbadensis* leaf juice, Bisabolol, *Cocos Nucifera* (coconut) oil, *Gardenia Tahitensis* flower, *Glycine soja* (soybean) oil, *Ribee Nigrum* (black current) seed oil, Sucrose Cocoate, *Glycine soja* (soybean) sterol, tocopherol, tocopheryl acetate, disodium EDTA, sorbitan stearate, PEG-40 stearate, phenoxyethanol, butylparaben, ethylparaben, methylparaben and propylparaben.

The plantain compositions of the invention include plantain compositions comprising an ointment formulation containing an extract derived from a plantain powder, and ointment formulations containing plantain in a particulate form.

The plantain composition can comprise plantain or an extract thereof, and at least one antibiotic, e.g., polymixin B sulfate, bacitracin zinc and/or neomycin. In a specific embodiment, the antibiotic can include at least one of polymixin B sulfate in an amount of 5000-10,000 U/g, bacitracin zinc in an amount of 200-600 IU/g, and neomycin base in an amount of 1.5-4 gm/g of the composition.

The plantain composition may include a cream base and plantain or plantain extract, e.g., from 0.5 weight % to 5 weight % of plantain powder, based on the weight of the composition.

The invention also contemplates a method of making a dermatological plantain composition, comprising dispersing plantain powder in an aqueous medium and mixing the resulting material for a predetermined time at elevated temperature to cause extraction of the plantain into the aqueous medium, recovering a supernatant from said material, and formulating the supernatant with a dermatologically acceptable carrier to produce said dermatological plantain composition.

In another aspect, the invention relates to a plantain cream composition, comprising the following ingredients in the specified weight percentages:
Water, 50-70 weight percent
Lactose, 0.5-5 weight percent
Urea, 0.5-5 weight percent
*Aloe Barbadensis* Leaf Juice, 0-0.1 weight percent
Disodium EDTA, 0-0.2 weight percent
Sodium Carboxymethyl Starch, 0-2 weight percent
Glycerin, 10-25 weight percent
DL-alpha Tocopheryl Nicotinate, 0-1 weight percent
Self-Emulsifying Wax NF, 0-6 weight percent
*Glycine Soja* (soybean) Oil (and) *Helianthus Annuus* (Hybrid Sunflower) Oil, 0-4 weight percent
Tocopheryl Acetate, 0-1 weight percent
*Butyrospermum Parkii* (Shea Butter) Fruit, 0-4 weight percent
*Cocos Nucifera* (Coconut) Oil, 0-4 weight percent
*Cocos Nucifera* (Coconut) Oil/*Aloe Barbadensis* Leaf Extract, 0-4 weight percent
*Glycine Soja* (Soybean) Oil (and) *Arnica Montana* Flower Extract (and) Tocopherol, 0-4 weight percent
Bisabolol, 0-1 weight percent
Hydrogenated Coconut Oil (and) *Gardenia Tahitensis* Flower (and) Tocopherol, 0.5-2.5 weight percent
*Oenothera Biennis* (Evening Primrose) Flower Oil, 0.1-1 weight percent
Camelina Oil, 0.1-1 weight percent
Benzyl PCA (and) Phenoxyethanol, 0.2-2 weight percent
*Plantago Major* Leaf, 0.1-5 weight percent
Mica (and) Titanium Dioxide (and) Iron Oxides, 0-2 weight percent
wherein the weight percent of all ingredients totals to 100 weight percent.

Another aspect of the invention relates to a plantain cream composition, comprising the following ingredients in the specified weight percentages:

| Ingredient | Wt % |
| --- | --- |
| Water | 50-65 |
| Lactose | 0-5 |
| Urea | 0-5 |
| *Aloe Barbadensis* Leaf Juice | 0-0.5 |
| Disodium EDTA | 0-0.5 |
| Sodium Carboxymethyl Starch | 0-2.5 |
| Glycerin | 8-22 |
| DL-alpha Tocopheryl Nicotinate | 0-2 |
| Self-Emulsifying Wax NF | 0-5 |
| *Glycine Soja* (soybean) Oil (and) *Helianthus Annuus* (Hybrid Sunflower) Oil | 0-5 |
| Tocopheryl Acetate | 0-2 |
| *Butyrospermum Parkii* (Shea Butter) Fruit | 0-5 |
| *Cocos Nucifera* (Coconut) Oil | 0-5 |
| *Prunus Amygdalus Dulcis* (Sweet Almond) Oil (and) Hydrogenated Vegetable Oil | 0-5 |
| *Glycine Soja* (Soybean) Oil (and) *Arnica Montana* Flower Extract (and) Tocopherol | 0-5 |
| Bisabolol | 0-0.5 |
| Hydrogenated Coconut Oil (and) *Gardenia Tahitensis* Flower (and) Tocopherol | 0-2.5 |
| *Oenothera Biennis* (Evening Primrose) Flower Oil | 0-1.5 |
| Jojoba Oil | 0-2 |
| Benzyl PCA (and) Phenoxyethanol | 0-2.5 |
| *Plantago Major* Leaf | 0.5-10 |
| Mica (and) Titanium Dioxide (and) Iron Oxides | 0-5 | wherein the weight percent of all ingredients totals to 100 weight percent.

A further aspect of the invention relates to a plantain ointment composition, comprising the following ingredients in the specified weight percentages:

| Ingredient | Wt % |
| --- | --- |
| Purified Water | 25-50 |
| Glycerin | 8-26 |
| Lactose | 0-5 |
| Urea | 0-5 |
| Sucrose Cocoate | 0-2.5 |
| *Aloe Barbadensis* Leaf Juice | 0-0.5 |
| *Butyrospermum Parkii* (Shea Butter) Fruit | 0-4 |
| *Theobroma Cacao* (Cocoa) Seed Butter | 0-4 |
| *Helianthus Annuus* (Hybrid Sunflower) Oil | 0-4 |
| Tocopheryl Acetate | 0-1.5 |
| Self-Emulsifying Wax | 0-10.5 |
| *Glycine Soja* (Soybean) Oil & *Arnica Montana* Flower Extract & Tocopherol | 0-5 |
| *Glycine Soja* (Soybean) Sterol | 0-2 |
| *Plantago Lanceolata* Leaf Extract | 2-20 |
| Disodium EDTA | 0-0.5 |
| Bisabolol | 0-0.5 |
| Phenoxyethanol, Methylparaben, Ethylparaben, Propylparaben, Butylparaben | 0-5 |
| Hydrogenated Coconut Oil & *Gardenia Tahitensis* Flower & Tocopherol | 0-5 |
| Sorbitan Stearate | 0-2.5 |
| PEG-40 Stearate | 0-2.5 |
| *Ribes Nigrum* (Black Currant) Seed Oil | 0-4 |
| Corn Starch Modified | 0-15 | wherein the weight percent of all ingredients totals to 100 weight percent.

It will be recognized at the compositions of the invention can be highly varied in character, and such compositions can be aqueous or non-aqueous, of dry powder form, or of liquid, paste, gel, solution or suspension form, in various embodiments. Illustrative compositions may be formulated as salves, ointments, lotions, rinses, aerosolized sprays, or other suitable compositional forms.

In simple powder/water formulations, concentrations of *Plantago major* powder are used that produce a paste-like or poultice consistency that is readily applied to the skin.

In another embodiment of the invention, the *Plantago major* powder is formulated in an aqueous composition containing other ingredients that enhance its application to and retention by the skin. Such other ingredients may include humectants, antioxidants, skin cleaning agents, essential oils, other plant extracts, preservatives, additional cosmetic ingredients, colorants, etc. In general, such additional ingredients may constitute from about 5 to about 99 weight % of the overall formulation, and may be formulated as desired for a specific application of the composition to the skin of an individual.

The individual subject may be a human, or other animal such as a horse, dog, cat, etc.

The compositions of the invention are usefully applied at any suitable intervals that effectuate diminution of the scarring and/or wrinkling of the individual's skin. In various embodiments, the composition can be applied at intervals of 1-12 times per week, for a period of 3-50 weeks or more, as may be necessary or desirable in a given instance to effectuate the remediation of the skin to the desired extent.

In a specific embodiment, the invention contemplates the use of plantain as an active ingredient in a burn ointment composition that is topically applied to the afflicted skin area.

In an illustrative burn ointment composition, the invention contemplates plantain in combination with ingredients including *Aloe Barbadensis* leaf juice, sunflower oil, Shea butter and tocopherol.

The burn ointment in another embodiment includes, in addition to plantain, petrolatum, *Aloe Barbadensis* leaf juice, *Helianthus Annuus* (hybrid sunflower) oil, *Butyrospermum Parkii* (Shea butter), fruit *Theobroma Cacao* (Cocoa) seed butter, *Persea Gratissima* (Avocado) oil, *Arnica Montana* flower extract, *Gardenia Tahitensis* flower, beeswax, Tocopherol (Vitamin E), Bisabolol (from Chamomile), *Eugenia Caryophyllus* (Clove) flower oil, and menthol camphor.

Such burn ointment may be applied to cover the burn area on the skin surface, and be reapplied as often as needed, e.g., 4-6 times daily, for a period of 16-20 weeks or more, as necessary, depending on the extent and severity of the burn.

In one embodiment, the plantain composition is formulated as an ointment, containing the following ingredients identified in Table 1.

TABLE 1

| Plantain Composition Ingredients (Ointment) |
|---|
| Water |
| Glycerin |
| Plantain |
| Modified Cornstarch |
| Emulsifying Wax, NF |
| Lactose |
| Urea |
| *Helianthus Annuus* (Hybrid Sunflower) Oil |
| *Butyrospermum Parkii* (Shea Butter) Fruit |
| *Theobroma Cacao* (Cocoa) Seed Butter |
| *Arnica Montana* Flower Extract |
| *Aloe Barbadensis* Leaf Juice |
| Bisabolol |
| *Cocos Nucifera* (Coconut) Oil |
| *Gardenia Tahitensis* Flower |
| *Glycine Soja* (soybean) Oil |
| *Ribee Nigrum* (Black Current) Seed Oil |

TABLE 1-continued

| Plantain Composition Ingredients (Ointment) |
|---|
| Sucrose Cocoate |
| *Glycine Soja* (Soybean) Sterol |
| Tocopherol |
| Tocopheryl Acetate |
| Disodium EDTA |
| Sorbitan Stearate |
| PEG-40 Stearate |
| Phenoxyethanol |
| Butylparaben |
| Ethylparaben |
| Methylparaben |
| Propylparaben | wherein the respective ingredients may be present at any suitable proportions, in relation to one another, and wherein the weight percent amounts of all ingredients totals to 100 weight percent.

In another specific embodiment, the plantain composition is formulated as an ointment containing an extract derived from a plantain powder.

A further embodiment is constituted by a plantain composition that is formulated as an ointment containing plantain in a particulate form.

The plantain compositions of the invention can be formulated with other dermal treatment or cosmetic ingredients. In one embodiment, the plantain composition is formulated with one or more antibiotics, such as polymixin B sulfate in an amount of 5000-10,000 U/g, bacitracin zinc in an amount of 200-600 IU/g, and/or neomycin base in an amount of 1.5-4 gm/g.

The plantain composition can for example be constituted by a cream base of suitable character, as a vehicle for the plantain. Illustrative of such approaches are cream base compositions containing 4% by weight of plantain extract, cream base compositions containing 0.5% of plantain powder, and cream base compositions containing 5% of plantain powder, in which the plantain powder has been sifted or otherwise graded to remove coarser particles, and yield a plantain powder of suitable character for formulation purposes.

In one preparative technique, a plantain extract is obtained by dispersing a plantain powder in water and mixing the resulting material for an extended time at elevated temperature. The plantain powder/water fixture may for example, in a specific embodiment, consist of 6.7% plantain powder and 93.3% water that is mixed for approximately 2 hours at temperature of 70-75° C. The resulting slurry then is decanted or strained to remove the supernatant from the insoluble material, as the plantain extract. More generally, extraction may be carried out in any suitable manner, using aqueous or non-aqueous solvent extraction media, as appropriate to the desired form of the extract for use in plantain compositions of the invention.

In another embodiment, the plantain composition is formulated as a cream containing the ingredients specified in Table 2, wherein the term "Trade" identifies the ingredient by industrial or commercial designation, "INCI" identifies the ingredient by common or chemical name, and "%" refers to the weight percent of the ingredient in the composition.

TABLE 2

Plantain Composition (0.5% Plantain Cream)

| Trade | INCI | % |
|---|---|---|
| Water | Water | 60.31 |
| Pharmatose | Lactose | 2.00 |
| Urea | Urea | 2.00 |
| Veragel 200 | *Aloe Barbadensis* Leaf Juice | 0.04 |
| Versene NA | Disodium EDTA | 0.10 |
| Naturally Thik CS | Sodium Carboxymethyl Starch | 1.00 |
| Glycerin | Glycerin | 15.00 |
| Vitamin E Nicotinate | DL-alpha Tocopheryl Nicotinate | 0.50 |
| Polawax | Self-Emulsifying Wax NF | 4.00 |
| FloraSun 90 | *Glycine Soja* (soybean) Oil (and) *Helianthus Annuus* (Hybrid Sunflower) Oil | 2.00 |
| Vitamin E Acetate | Tocopheryl Acetate | 0.50 |
| Shea Butter | *Butyrospermum Parkii* (Shea Butter) Fruit | 2.00 |
| Cocoa Butter | *Cocos Nucifera* (Coconut) Oil | 2.00 |
| *Aloe* Butter | *Cocos Nucifera* (Coconut) Oil/*Aloe Barbadensis* Leaf Extract | 2.00 |
| *Arnica* Oil CLR | *Glycine Soja* (Soybean) Oil (and) *Arnica Montana* Flower Extract (and) Tocopherol | 2.00 |
| Bisabolol | Bisabolol | 0.05 |
| Monoi Butter | Hydrogenated Coconut Oil (and) *Gardenia Tahitensis* Flower (and) Tocopherol | 1.50 |
| Evening Primrose Oil | *Oenothera Biennis* (Evening Primerose) Flower Oil | 0.50 |
| *Camelina* Oil | *Camelina* Oil | 0.50 |
| Twincide A | Benzyl PCA (and) Phenoxyethanol | 1.00 |
| Plantain | *Plantago Major* Leaf | 0.50 |
| KTZ Interval Green | Mica (and) Titanium Dioxide (and) Iron Oxides | 0.50 |

Another cream formulation containing 5% plantain is specified in Table 3 below.

TABLE 3

Plantain Composition (5% Plantain Cream)

| Trade | INCI | % |
|---|---|---|
| Water | Water | 54.81 |
| Pharmatose | Lactose | 2.00 |
| Urea | Urea | 2.00 |
| Veragel 200 | *Aloe Barbadensis* Leaf Juice | 0.04 |
| Versene NA | Disodium EDTA | 0.10 |
| Naturally Thik CS | Sodium Carboxymethyl Starch | 1.50 |
| Glycerin | Glycerin | 15.00 |
| Vitamin E Nicotinate | DL-alpha Tocopheryl Nicotinate | 0.50 |
| Polawax | Self-Emulsifying Wax NF | 4.00 |
| FloraSun 90 | *Glycine Soja* (soybean) Oil (and) *Helianthus Annuus* (Hybrid Sunflower) Oil | 2.00 |
| Vitamin E Acetate | Tocopheryl Acetate | 0.50 |
| Shea Butter | *Butyrospermum Parkii* (Shea Butter) Fruit | 2.00 |
| Cocoa Butter | *Cocos Nucifera* (Coconut) Oil | 2.00 |
| Almond Butter | *Prunus Amygdalus Dulcis* (Sweet Almond) Oil (and) Hydrogenated Vegetable Oil | 2.00 |
| *Arnica* Oil CLR | *Glycine Soja* (Soybean) Oil (and) *Arnica Montana* Flower Extract (and) Tocopherol | 2.00 |
| Bisabolol | Bisabolol | 0.05 |
| Monoi Butter | Hydrogenated Coconut Oil (and) *Gardenia Tahitensis* Flower (and) Tocopherol | 1.50 |
| Evening Primrose Oil | *Oenothera Biennis* (Evening Primerose) Flower Oil | 0.50 |
| Jojoba Oil | Jojoba Oil | 0.50 |
| Twincide A | Benzyl PCA (and) Phenoxyethanol | 1.00 |
| Plantain | *Plantago Major* Leaf | 5.00 |
| KTZ Interval Green | Mica (and) Titanium Dioxide (and) Iron Oxides | 1.00 |

Yet another composition of the invention comprises a plantain ointment, having the composition set forth in Table 4 below.

TABLE 4

Plantain Ointment

| Purified Water | Purified Water | 37.810 |
|---|---|---|
| Glycerin | Glycerin | 15.000 |
| Pharmatose DCL-21 | Lactose | 2.000 |
| Urea | Urea | 2.000 |
| Tego-Soft | Sucrose Cocoate | 1.000 |
| *Aloe Vera* 200X | *Aloe Barbadensis* Leaf Juice | 0.040 |
| Shea Butter | *Butyrospermum Parkii* (Shea Butter) Fruit | 2.000 |
| Cocoa Butter | *Theobroma Cacao* (Cocoa) Seed Butter | 2.000 |
| FloraSun 90 | *Helianthus Annuus* (Hybrid Sunflower) Oil | 2.000 |
| Vitamin E Acetate | Tocopheryl Acetate | 0.500 |
| Polawax NF | Self-Emulsifying Wax | 8.000 |
| *Arnica* Oil CLR | *Glycine Soja* (Soybean) Oil & *Arnica Montana* Flower Extract & Tocopherol | 2.000 |
| Generol 122 | *Glycine Soja* (Soybean) Sterol | 0.500 |
| Plantain | *Plantago Lanceolata* Leaf Extract | 10.000 |
| Versene NA | Disodium EDTA | 0.100 |
| Bisabolol | Bisabolol | 0.050 |
| Phenonip | Phenoxyethanol, Methylparaben, Ethylparaben, Propylparaben, Butylparaben | 1.000 |
| *Monoi* Butter | Hydrogenated Coconut Oil & *Gardenia Tahitensis* Flower & Tocopherol | 1.500 |
| Arlacel 60 | Sorbitan Stearate | 1.000 |
| Myrj 52 | PEG-40 Stearate | 1.000 |
| Black Currant Oil | *Ribes Nigrum* (Black Currant) Seed Oil | 0.500 |
| DryFlo AF | Corn Starch Modified | 10.000 |

In still other embodiments of the invention, the compositions of the invention may contain as additional ingredients one or more of glucose, glucose oxidase, and lactose peroxidase.

In one illustrative embodiment, the composition of the invention includes the following ingredients listed in Table 5 below.

TABLE 5

| Ingredient |
| --- |
| Water |
| Glycerin |
| Plantain (*Plantago Major* Extract) |
| Sodium Carboxymethyl Starch |
| Emulsifying Wax |
| Lactose |
| *Helianthus Annus* (Hybrid Sunflower) Oil |
| *Butyrospermum Parkii* (Shea butter) Fruit |
| *Theobroma Cacao* (Cocoa) Seed Butter |
| *Arnica Montana* Flower Extract |
| *Aloe Vera* |
| Bisabolol |
| *Cocos Nucifera* (Coconut) Oil |
| *Glycine Soya* (Soybean Oil) |
| *Prunus Amygdalus Dulcis* (Sweet Almond) Oil |
| Hydrogenated Vegetable Oil |
| Tocopherol (Vitamin E) |
| *Gardenia Tahitensis* Flower Extract |
| Tocopheryl Acetate |
| Disodium EDTA |
| *Oenothera Biennis* (Evening Primrose) Oil |
| *Simmondsia Chinesis* (Jojoba) Seed Oil |
| Glucose |
| Glucose Oxidase |
| Lactose Peroxidase |
| Titanium Dioxide |
| Iron Oxide |
| Mica |

The invention therefore contemplates a wide variety of plantain-based compositions containing *Plantago major* or *Plantago Lanceolata* and having efficacy for treatment of skin to reduce scarring, including treatment of preexisting scarring to minimize the size, color, and severity of the scarring to at least partially restore skin to an undamaged or less damaged state, as well as treatment of skin to reverse wrinkling, to treat burns, and to minimize and ameliorate skin damage due to wounds, stretch marks, aging spots, sunburn, stitches, and the like.

The compositions of the invention as described herein may alternatively comprise, consist, or consist essentially of, any combinations of any of the ingredients herein disclosed, and such compositions of the invention may be defined in specific embodiments of the invention as excluding any of various excipients or other ingredients herein disclosed. It will therefore be recognized that the invention contemplates all variations and permutations of the various ingredients described herein, in specific embodiments of the invention.

The compositions of the invention may be formulated in a crème base, oil, oil in water emulsion, liquid, gel, paste, powder, or any other form that is suitable for application to the skin of a user. The invention contemplates delivery of the *Plantago major* or *Plantago Lanceolata* composition in a patch, bandage, or any other article or material that can be placed in contact with the skin. The invention contemplates humans as well as other mammalian and non-mammalian animals as subjects whose skin can be beneficially treated with compositions of the invention, e.g., human clinical and human consumer usage, as well as veterinary usage.

The amounts of the active ingredient *Plantago major* or *Plantago Lanceolata* may in various embodiments of the invention be characterized as being in a range of concentration by weight, based on the total weight of the skin treatment composition. For example, in specific ranges, the lower limit of concentration may variously be 0.5, 1, 2, 3, 4, 5, 6, 7, 8, 9, 10, 12, 15, 18, 20, 25, 30, 35, or 40% by weight, and the upper limit may be variously be 4, 5, 6, 7, 8, 9, 10, 12, 15, 18, 20, 25, 30, 35, 40, 50, 60, 70, 75, 80, 90 or approaching 100% by weight of the total weight of the composition. It will be further appreciated that sub-ranges of concentration within specified concentration ranges may independently be included in smaller concentration ranges, within the scope of the invention, and that ranges of concentration specifically excluding a concentration or concentrations are included in the invention, and sub-ranges excluding either or both of concentration limits of specified ranges are also included in the invention.

The compositions of the invention may be formulated to include other skin care or protective products or ingredients, so that the overall composition is most suitably prepared for specific skin care applications.

Although the invention has been specifically exemplified with reference to *Plantago major* or *Plantago Lanceolata* powder formulations, it will recognized that compositions of the invention can utilize such plantain actives in a variety of forms, including leaves, stems, extracts, juices, pulps, finely divided forms of the plant, or other forms as otherwise may be effective for a specific formulation and use.

Referring now to the drawings, FIGS. 1-19 show a series of before and after photographs evidencing the efficacy of plantain compositions as utilized in accordance with the present invention.

FIG. 1 is a photograph of a hypertrophic 10-year-old facial scar at the right temple of the illustrated individual, as it appeared prior to treatment with a composition according to the present invention.

Figure 2:
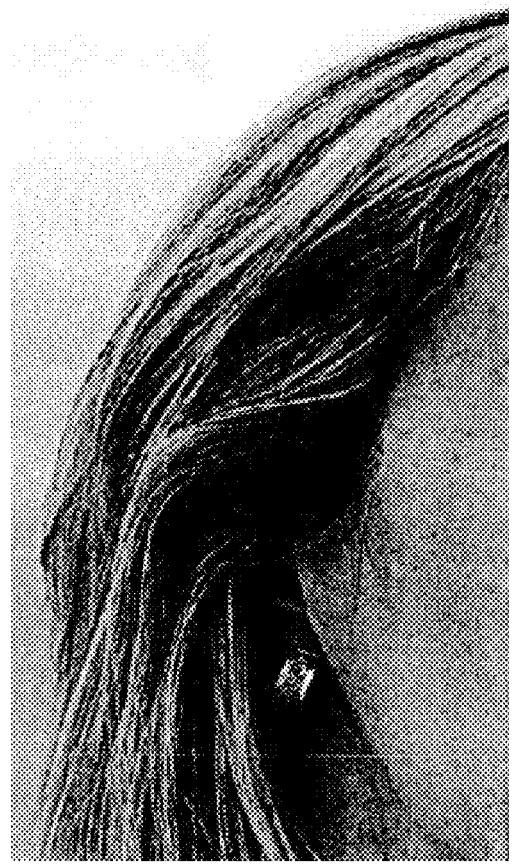
FIG. 2 is a photograph of the individual of FIG. 1, showing the appearance of the scar at the individual's temple, after 2 months of treatment involving application of a composition according to the present invention, at intervals of three-four times per week.

FIG. 2 is a photograph of the individual of FIG. 1, showing the appearance of the scar at the individual's temple, after 2 months of treatment involving application of a composition according to the present invention, at intervals of three-four times per week.

The individual shown in FIG. 1 is a 48 year old female who was treated with a composition containing the *Plantago major* powder. The composition contained *Plantago major* powder in an amount of 40-60% by weight and water in an amount of 1-15%, based on the total weight of the composition. The composition was applied as a paste to the scar area of such individual at intervals of every other day, and in each application was left on the skin of the individual for period of approximately 8-10 hours.

A comparison of FIGS. 1 and 2 shows that the scar was markedly reduced in visual prominence by treatment with the *Plantago major* powder composition.

The individual shown in FIGS. 1 and 2 during the treatment of the hypertrophic facial scar on her right temple with the composition of the present invention noted that the right-side "crows feet" wrinkles on her face were markedly reduced as a result of the application of the plantain composition to the right temple area for treatment of the scar. The left temple crows feet wrinkles therefore served as an intrafacial control during the period of the administration of the composition to the right temple area. It therefore was discovered that the crows feet markings on the face of the individual were markedly reduced in relation to the crows feet on the left temple of the subject.

Figure 3:
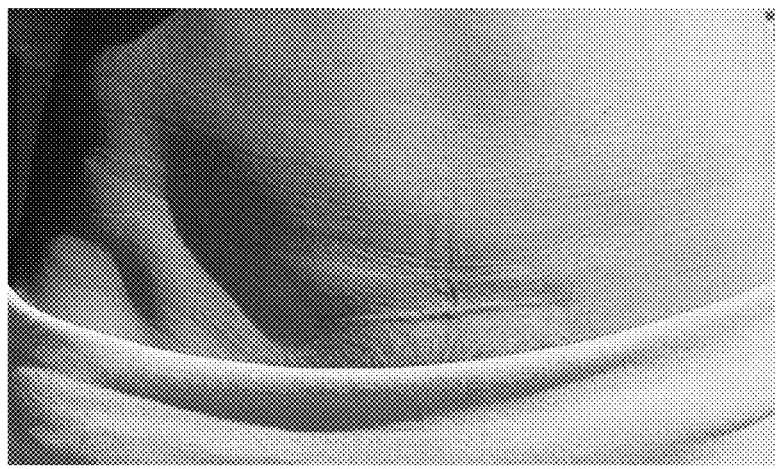
FIG. 3 is a 5-inch long, 18 month old myomectomy ("C-section") keloid scar of an individual, prior to treatment with a composition according to the present invention.

FIG. 3 is a 5-inch long, 18 month old myomectomy ("C-section") keloid scar of an individual, prior to treatment with a composition according to the present invention.

Figure 4:
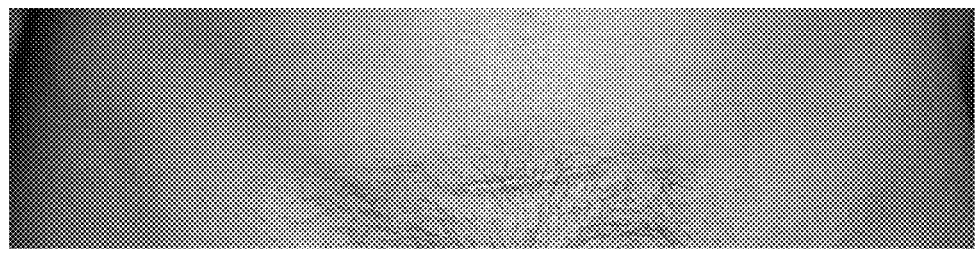
FIG. 4 is a photograph of the same individual of FIG. 3, showing the remediation of the scar after a treatment regimen involving application of a composition according to the present invention, with the myomectomy keloid scar being reduced in size to 1.5 inches, after one month of treatment for 8 hours per day using the composition of the invention.

FIG. 4 is a photograph of the same individual of FIG. 3, showing the remediation of the scar after a treatment regimen involving application of a composition according to the present invention, with the myomectomy keloid scar being reduced in size to 1.5 inches, after one month of treatment for 8 hours per day using the composition of the invention.

The individual shown in the photographs of FIGS. 3 and 4 was a 48-year old female in normal health. Such individual was treated with a *Plantago major* powder composition of the invention, formulated as containing 40-60% of such powder and 1-15% of water, as a paste that was applied to the scar area at intervals of 3 to 4 times per weeks, each time being retained on the skin for a period of 8 to 10 hours. This treatment was continued for a period of 2 months.

A comparison of the FIG. 3 and FIG. 4 photographs shows that there was marked reduction of the C-section scar by application of the *Plantago major* powder composition, and the scarring markedly decreased in coloration as a result of such treatment.

Figure 5:
FIG. 5 is a photograph of a 50 year old male with a suture scar resulting from a gash to the forehead.

FIG. 5 is a photograph of a 50 year old male with a suture scar resulting from a gash to the forehead, the scar being visible in the FIG. 5 photograph in the center of the forehead of the individual.

Figure 6:
FIG. 6 is a photograph of the scar area of the same individual shown in FIG. 5, after three weeks treatment with a composition of the present invention.

FIG. 6 is a photograph of the scar area of the same individual shown in FIG. 5, after three weeks treatment with a composition of the present invention, showing the scar area to be substantially free of visible scarring. The composition employed in the treatment of this individual was a *Plantago major* powder composition of the invention, formulated as containing 40-60% of such powder and 1-15% of water, as a paste that was applied to the forehead area of the suture scar.

Figure 7:
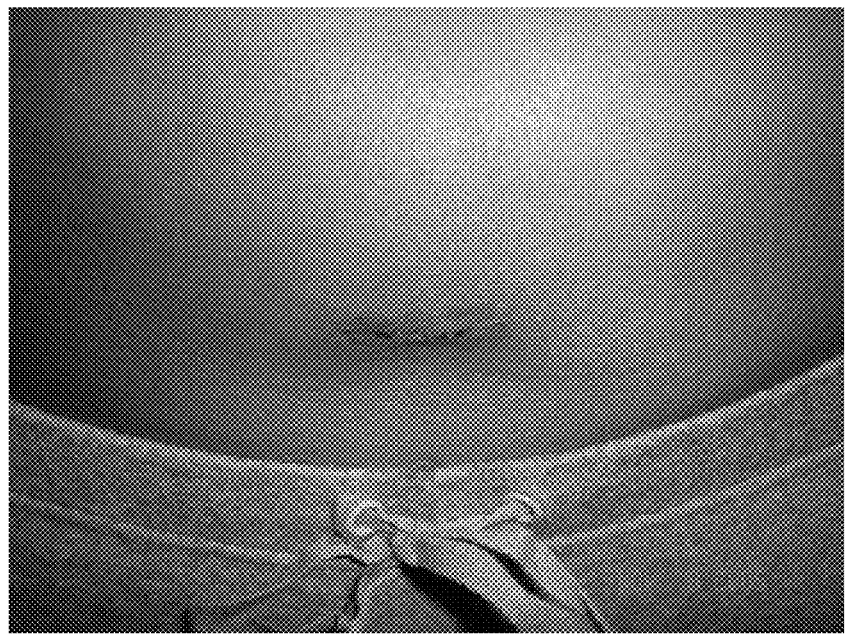
FIG. 7 is a photograph of a surgical wound from laproscopic hysterectomy performed on a 46-year old female.

FIG. 7 is a photograph of a surgical wound from laproscopic hysterectomy performed on a 46-year old female.

Figure 8:
FIG. 8 is a photograph of the wound area of the individual whose wound is shown in FIG. 7, evidencing the minimal scarring after treatment with a composition of the present invention after treatment for 1 month, four times a week.

FIG. 8 is a photograph of the wound area of the individual whose wound is shown in FIG. 7, evidencing the minimal scarring after treatment with a composition of the present invention after treatment for 1 month, four times a week. The composition employed in the treatment of this individual was a *Plantago major* powder composition of the invention, formulated as containing 40-60% of such powder and 1-15% of water, as a paste that was applied to the laproscopic wound area.

Figure 9:
FIG. 9 is a photograph of a 46 year old male with a deep abrasion from a motorcycle accident, who was treated with a composition of the present invention.

FIG. 9 is a photograph of a 46 year old male with a deep abrasion from a motorcycle accident, who was treated with a composition of the present invention.

Figure 10:
FIG. 10 is a photograph of the individual shown in FIG. 9, exhibiting the absence of scarred skin after treatment with a composition of the present invention, after two weeks daily use for 12 hours.

FIG. 10 is a photograph of the individual shown in FIG. 9, exhibiting the absence of scarred skin after treatment with a composition of the present invention, after two weeks daily use for 12 hours. The composition employed in the treatment of this individual was a *Plantago major* powder composition of the invention, formulated as containing 40-60% of such powder and 1-15% of water, as a paste that was applied to the wound area.

Figure 11:
FIG. 11 is a photograph of an individual one year after a broken neck operation, showing the neck scar of such individual.

FIG. 11 is a photograph of an individual one year after a broken neck operation, showing the neck scar of such individual.

Figure 12:
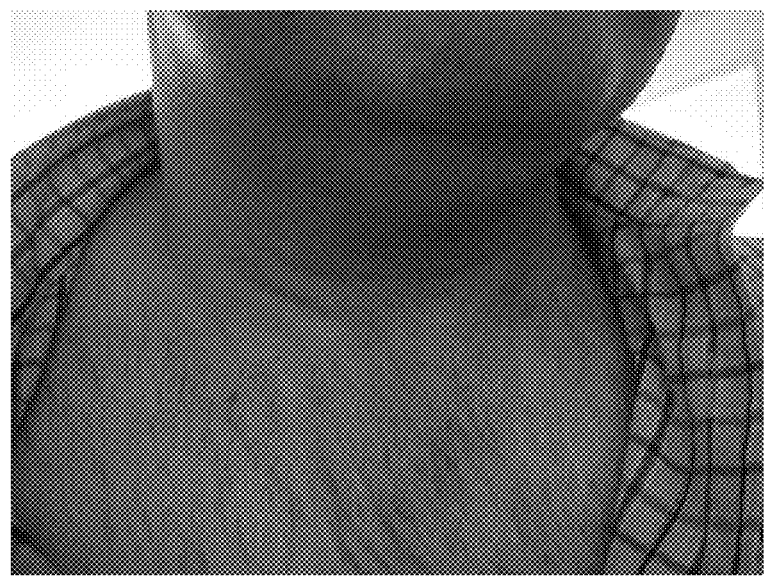
FIG. 12 is a photograph of the individual shown in FIG. 11, exhibiting the diminution of the neck scar after treatment with a composition of the present invention for two months, three to four times a week.

FIG. 12 is a photograph of the individual shown in FIG. 11, exhibiting the diminution of the neck scar after treatment with a composition of the present invention for two months, three to four times a week. The composition employed in the treatment of this individual was a *Plantago major* powder composition of the invention, formulated as containing 40-60% of such powder and 1-15% of water, as a paste that was applied to the neck scar.

Figure 13:
FIG. 13 is a photograph of a six-month-old scar on the knee of a subject, prior to treatment with a composition according to the present invention.

FIG. 13 is a photograph of a six-month-old scar on the knee of a subject, prior to treatment with a composition according to the present invention.

Figure 14:
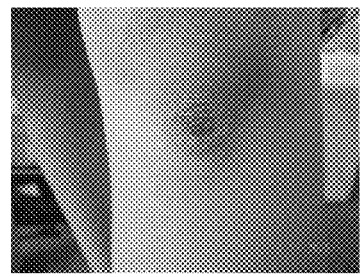
FIG. 14 is a photograph of the same individual shown in FIG. 13, illustrating the diminution of the scar of FIG. 13, midway through a treatment regimen involving a composition of the present invention as applied at intervals to the scar locus for four months.

FIG. 14 is a photograph of the same individual shown in FIG. 13, illustrating the diminution of the scar of FIG. 13, after a treatment regimen involving a composition of the present invention applied to the scar locus for four months.

Figure 15:
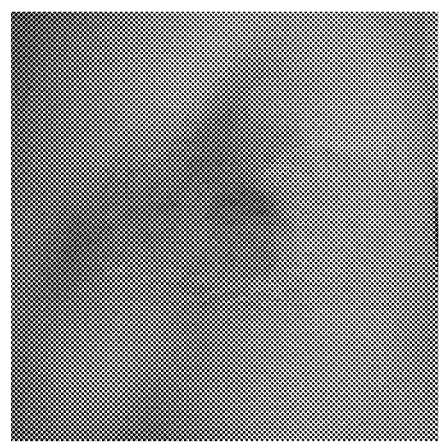
FIG. 15 is a photograph of the same individual shown in FIG. 13, illustrating the diminution of the scar of FIG. 13 after 6 months of 4-times per week of treatment with the composition of the invention.

FIG. 15 is a photograph of the same individual shown in FIG. 13, illustrating the diminution of the scar of FIG. 13 after 6 months of 4-times per week of treatment with the composition of the invention.

The individual shown in FIGS. 13-15 was a 29 year old individual, whose knee was scarred six months prior to the time that the photograph of FIG. 13 was taken, in an accident involving a fall. This individual was treated with a composition containing *Plantago major* powder in an amount of 40-60% and water in the amount of 1-15% by weight, based on the total weight of the composition. The composition was applied to the scarred area, each time being maintained on the skin at the scar locus for a period of 8 to 10 hours.

Figure 16:
FIG. 16 is a photograph of a 21-year old female's foot showing a third degree hot wax burn prior to treatment.

FIG. 16 is a photograph of a 21-year old female's foot showing a third degree hot wax burn prior to treatment.

Figure 17:
FIG. 17 is a photograph of the foot of the 21-year old female shown in FIG. 16, after treatment with a composition of the present invention daily for two weeks.

FIG. 17 is a photograph of the foot of the 21-year old female shown in FIG. 16, after treatment with a composition of the present invention daily for two weeks. The composition employed in the treatment of this individual was a *Plantago major* powder composition of the invention, formulated as containing 40-60% of such powder and 1-15% of water, as a paste that was applied to the burn. FIG. 17 shows a complete remission of the burn and restoration of unblemished skin.

The foregoing before-and-after photographs of FIGS. 1-17 show the marked improvement that is achieved in relatively short time by administration of the compositions of the present invention, in reducing the size and coloration of scarring and at least partially restoring skin to an undamaged, undeteriorated state.

Figure 18:
FIG. 18 is a photograph of crows feet and under eye crease of 49 year old female.

FIG. 18 is a photograph of crows feet and under eye crease of 49 year old female.

Figure 19:
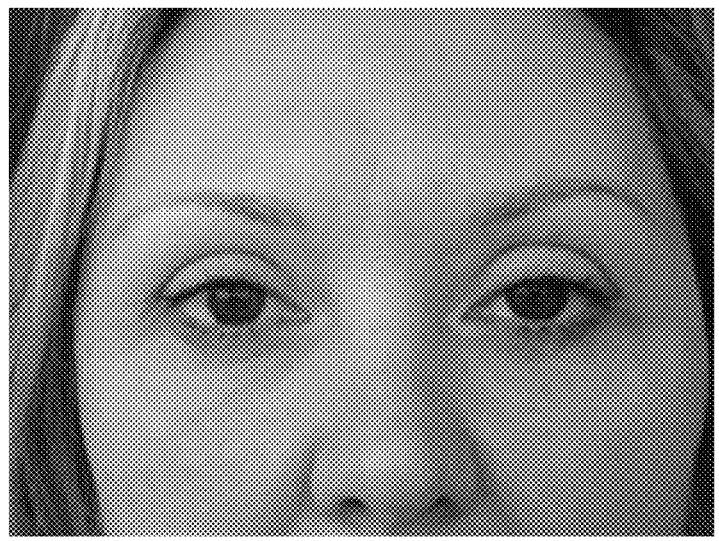
FIG. 19 is a photograph of the female subject shown in FIG. 18, after overnight treatment with a 100% plantain composition.

FIG. 19 is a photograph of the female subject shown in FIG. 18, after overnight treatment with a 100% plantain composition applied to the eye regions of the individual.

A comparison of FIGS. 18 and 19 evidences the latter photograph as showing a dramatic reduction in crow's feet and eye crease wrinkling, thereby demonstrating the efficacy of the plaintain compositions of the invention for reducing wrinkling.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A topical composition effective for treating scarred and/or burned skin of a human in need thereof, wherein the topical composition comprises:
   water, 50-70 wt %;
   Glycerin, 8-25 wt %;
   *Plantago major* leaf power and/or extract thereof, 0.1-10 wt %;
   Tocopherol and/or tocopheryl acetate, >0-1.5 wt %;
   *Aloe barbadensis* leaf juice, >0-0.5 wt %;
   Cocoa butter, >0-5 wt %; and
   Shea butter, >0-4 wt %.

2. A topical composition as claimed in claim 1 wherein said *Plantago major* comprises about 0.50 to about 10% by weight of the total weight of the composition.

3. A topical composition as claimed in claim 1 wherein said tocopherol and/or tocopheryl acetate comprises about 0.50% by weight of the total weight of the composition.

4. A topical composition as claimed in claim 1 wherein said *Aloe barbadensis* leaf juice comprises about 0.04% by weight of the total weight of the composition.

5. A topical composition as claimed in claim 1 wherein said Cocoa butter comprises about 2.0% by weight of the total weight of the composition.

6. A topical composition as claimed in claim 1 wherein said Shea butter comprises about 2.0% by weight of the total weight of the composition.

7. A method for treating scarred and/or burned skin of a human in need thereof comprising applying an effective amount of the topical composition according to claim 1 to said skin.

8. A method for treating scarred and/or burned skin of a human in need thereof comprising applying an effective amount of the topical composition according to claim 2 to said skin.

9. A method for treating scarred and/or burned skin of a human in need thereof comprising applying an effective amount of the topical composition according to claim 3 to said skin.

10. A method for treating scarred and/or burned skin of a human in need thereof comprising applying an effective amount of the topical composition according to claim 4 to said skin.

11. A method for treating scarred and/or burned skin of a human in need thereof comprising applying an effective amount of the topical composition according to claim 5 to said skin.

12. A method for treating scarred and/or burned skin of a human in need thereof comprising applying an effective amount of the topical composition according to claim 6 to said skin.

* * * * *